United States Patent
Enomoto

(10) Patent No.: US 11,064,885 B2
(45) Date of Patent: Jul. 20, 2021

(54) MEDICAL TELEMETER, MEDICAL SYSTEM, AND METHOD OF CONTROLLING MEDICAL TELEMETER

(71) Applicant: NIHON KOHDEN CORPORATION, Tokyo (JP)

(72) Inventor: Yoshinori Enomoto, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 129 days.

(21) Appl. No.: 14/865,989

(22) Filed: Sep. 25, 2015

(65) Prior Publication Data

US 2016/0100759 A1 Apr. 14, 2016

(30) Foreign Application Priority Data

Oct. 10, 2014 (JP) .............................. JP2014-209368

(51) Int. Cl.
| | |
|---|---|
| *H04Q 9/00* | (2006.01) |
| *G08C 17/02* | (2006.01) |
| *H04Q 9/14* | (2006.01) |
| *G16H 40/67* | (2018.01) |
| *G16H 40/63* | (2018.01) |
| *A61B 5/00* | (2006.01) |

(52) U.S. Cl.
CPC ............ *A61B 5/0015* (2013.01); *G16H 40/63* (2018.01); *G16H 40/67* (2018.01); *A61B 5/746* (2013.01)

(58) Field of Classification Search
CPC ..... H04W 88/02; H04W 48/18; H04W 48/16; H04W 72/08
See application file for complete search history.

(56) References Cited

U.S. PATENT DOCUMENTS

| | | | | |
|---|---|---|---|---|
| 6,424,157 | B1 * | 7/2002 | Gollomp | G01R 31/006 320/132 |
| 2004/0172302 | A1 * | 9/2004 | Martucci | A61B 5/0002 705/2 |
| 2004/0193453 | A1 * | 9/2004 | Butterfield | A61M 5/172 705/2 |
| 2005/0060001 | A1 * | 3/2005 | Singhal | A61N 1/37264 607/19 |

(Continued)

FOREIGN PATENT DOCUMENTS

| | | | |
|---|---|---|---|
| JP | 2009-514332 A | 5/2008 | |
| JP | 2009-072962 A | 4/2009 | |

(Continued)

OTHER PUBLICATIONS

Japanese Office Action issued in Patent Application No. JP-2014-209368 dated Mar. 14, 2018.

*Primary Examiner* — Joseph H Feild
*Assistant Examiner* — Pameshanand Mahase
(74) *Attorney, Agent, or Firm* — Pearne & Gordon LLP

(57) ABSTRACT

A medical telemeter includes: a displaying section which is configured to display information; a storing section which is configured to store patient information that is information of a patient who uses the medical telemeter; and a controller which, when a predetermined event occurs, is configured to read the patient information stored in the storing section, and is configured to cause the displaying section to display a confirmation message that is based on the patient information.

12 Claims, 10 Drawing Sheets

(56) References Cited

U.S. PATENT DOCUMENTS

| | | | |
|---|---|---|---|
| 2006/0268319 A1* | 11/2006 | Winkel | G06F 21/35 358/1.15 |
| 2007/0267475 A1* | 11/2007 | Hoglund | G06F 19/327 235/375 |
| 2009/0058636 A1* | 3/2009 | Gaskill | A61N 1/37282 340/539.11 |
| 2009/0184842 A1 | 7/2009 | Baldus et al. | |
| 2009/0231124 A1* | 9/2009 | Klabunde | A61B 5/0205 340/539.12 |
| 2010/0328076 A1* | 12/2010 | Kyle | G06F 19/327 340/573.1 |
| 2011/0043366 A1 | 2/2011 | Osone et al. | |
| 2011/0080293 A1 | 4/2011 | Tanishima et al. | |
| 2012/0065477 A1* | 3/2012 | Enomoto | A61B 5/0006 600/300 |
| 2012/0068855 A1* | 3/2012 | Matsumura | A61B 5/0006 340/870.02 |
| 2014/0275819 A1* | 9/2014 | Kassem | A61B 5/031 600/301 |
| 2016/0019345 A1* | 1/2016 | Peguero | G06F 19/322 340/870.16 |

FOREIGN PATENT DOCUMENTS

| | | |
|---|---|---|
| JP | 2011-041769 A | 3/2011 |
| JP | 2011-098189 A | 5/2011 |
| JP | 2012-075854 A | 4/2012 |

* cited by examiner

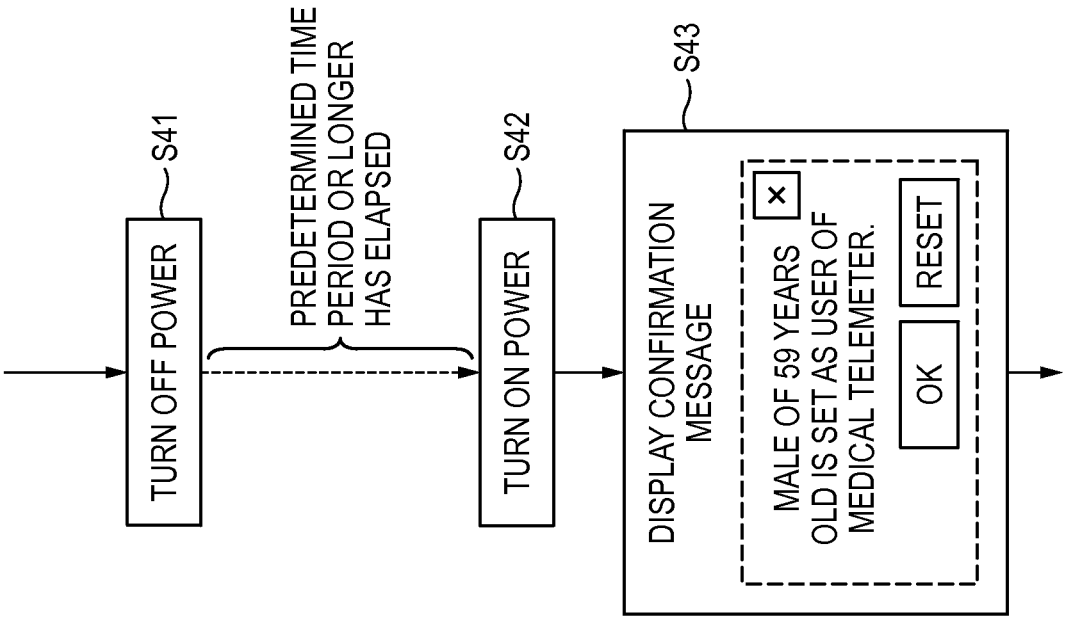
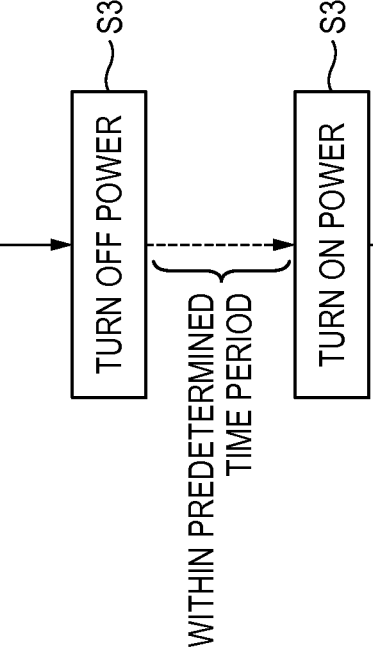

MEDICAL TELEMETER, MEDICAL SYSTEM, AND METHOD OF CONTROLLING MEDICAL TELEMETER

CROSS-REFERENCE TO RELATED APPLICATION(S)

This application is based upon and claims the benefit of priority from prior Japanese patent application No. 2014-209368, filed on Oct. 10, 2014, the entire contents of which are incorporated herein by reference.

BACKGROUND

The presently disclosed subject matter relates to a medical telemeter, a medical system, and a method of controlling a medical telemeter.

Recently, a medical telemeter which can bidirectionally wirelessly communicate with a central monitor is widely used. In such a medical telemeter, it is important to set correctly and surely information of a patient (for example, the name of a patient) (hereinafter, such information is referred to as patient information). When patient information is not correctly set in a medical telemeter, there occur troubles such as that a patient is misidentified.

JP-T-2008-514332 discloses a technique for setting patient information in a medical telemeter. JP-T-2008-514332 discloses a patient-side device in which the name of a patient (hereinafter, the name is referred to as the patient name) can be set in addition to the identification number of the patient, by a central monitor (Paragraph 0017, etc.).

In a medical telemeter, patient information must be correctly set every time when a patient who uses the medical telemeter is changed. Usually, a lighting device for illuminating a screen of a medical telemeter is not always turned ON, and the turn-OFF time of the lighting device is longer than the turn-ON time. Moreover, it is often that, in order to meet a request of miniaturization, a screen of a medical telemeter is not large. Therefore, a display of the patient name or the like which is set in a medical telemeter is sometimes too small and hardly seen. Because of such circumstances, there is a possibility that a medical telemeter in which patient information is not correctly set is continued to be used.

As described above, JP-T-2008-514332 discloses the configuration for allowing the central monitor to set the patient name and the like in the patient-side device. However, JP-T-2008-514332 suggests or teaches nothing about adequate confirmation of the set patient information.

That is, the related art including the technique disclosed in JP-T-2008-514332 has a problem in that patient information which is set in a medical telemeter cannot be adequately confirmed.

SUMMARY

The presently disclosed subject matter may provide a medical telemeter, medical system, and method of controlling a medical telemeter in which set patient information can be adequately confirmed.

The medical telemeter may comprise: a displaying section which is configured to display information; a storing section which is configured to store patient information that is information of a patient who uses the medical telemeter; and a controller which, when a predetermined event occurs, is configured to read the patient information stored in the storing section, and is configured to cause the displaying section to display a confirmation message that is based on the patient information.

BRIEF DESCRIPTION OF THE DRAWINGS

FIGS. 8A and 8B are diagrams showing the process of displaying the confirmation message by the medical telemeter 100 of Embodiment 1.

DETAILED DESCRIPTION OF EXEMPLARY EMBODIMENTS

Embodiment 1

Hereinafter, the presently disclosed subject matter will be described by way of an embodiment thereof. However, the following embodiment is not intended to limit the presently disclosed subject matter as defined in the appended claims, and all combinations of features described in the embodiment are not always essential to solving means of the presently disclosed subject matter.

Figure 1:
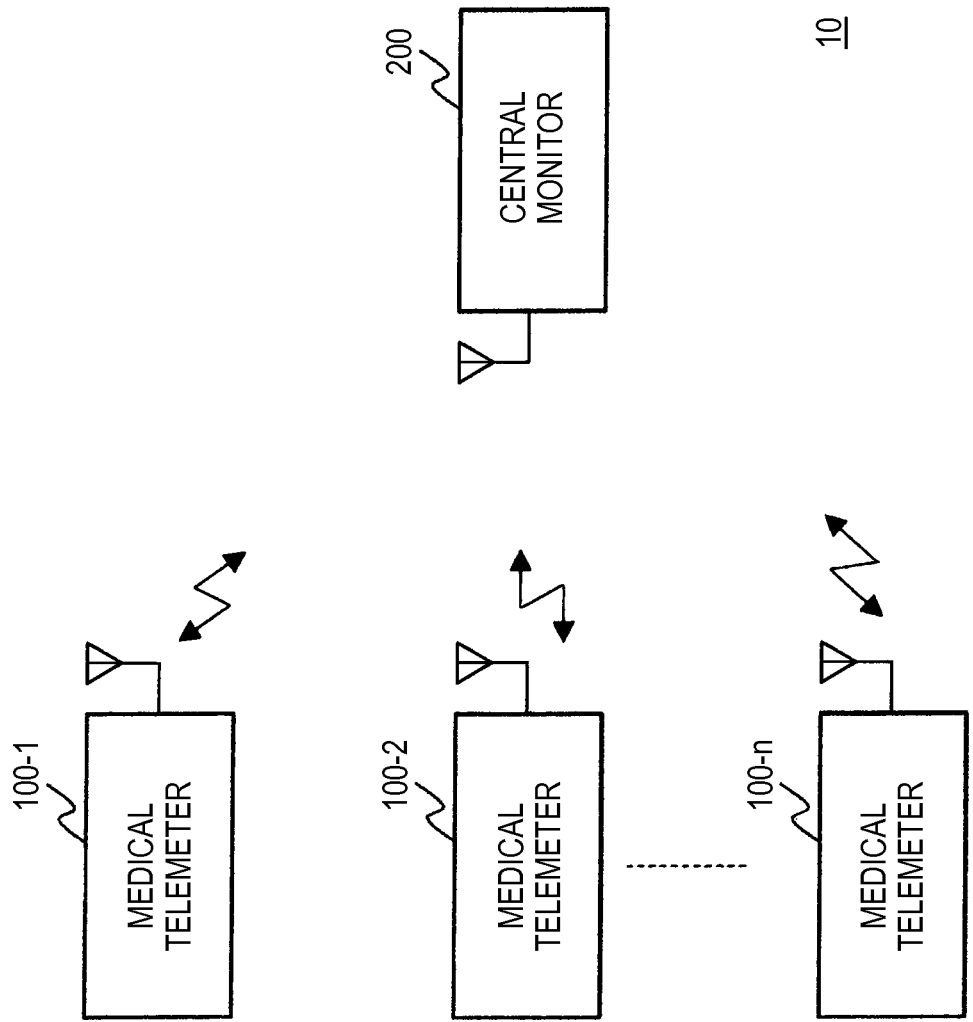
FIG. 1 is a conceptual diagram showing the configuration of a medical system 10 of Embodiment 1.

FIG. 1 is a conceptual diagram showing the configuration of a medical system 10 of the embodiment. The medical system 10 is a system which is used mainly in a hospital. The medical system 10 includes a plurality of medical telemeters 100 (100-1, 100-2, . . . , 100-$n$) which transmit biological data (biological information such as an electrocardiogram and the respiratory rate) of a patient, and a central monitor 200 which receives and displays the biological data transmitted from the medical telemeters 100 (100-1, 100-2, . . . , 100-$n$). In the following description, when one of the medical telemeters 100 (100-1, 100-2, . . . , 100-$n$) is not specified, the medical telemeter is referred to as "medical telemeter 100."

The medical telemeter 100 and the central monitor 200 are configured so that they can mutually transmit and receive data by wireless communication. For example, the medical telemeter 100 and the central monitor 200 transmit and receive data by a wireless communication process which uses the WIFI standard, and which performs data transmission/reception through access points. Alternatively, the medical telemeter 100 may be configured so as to, unlike the configuration shown in FIG. 1, have two antennas (a transmission antenna and a reception antenna), and perform transmission and reception through the transmission and reception antennas. Namely, the medical telemeter 100 and the central monitor 200 may employ any kind of communication technique as far as data can be bidirectionally transmitted and received.

Figure 2:
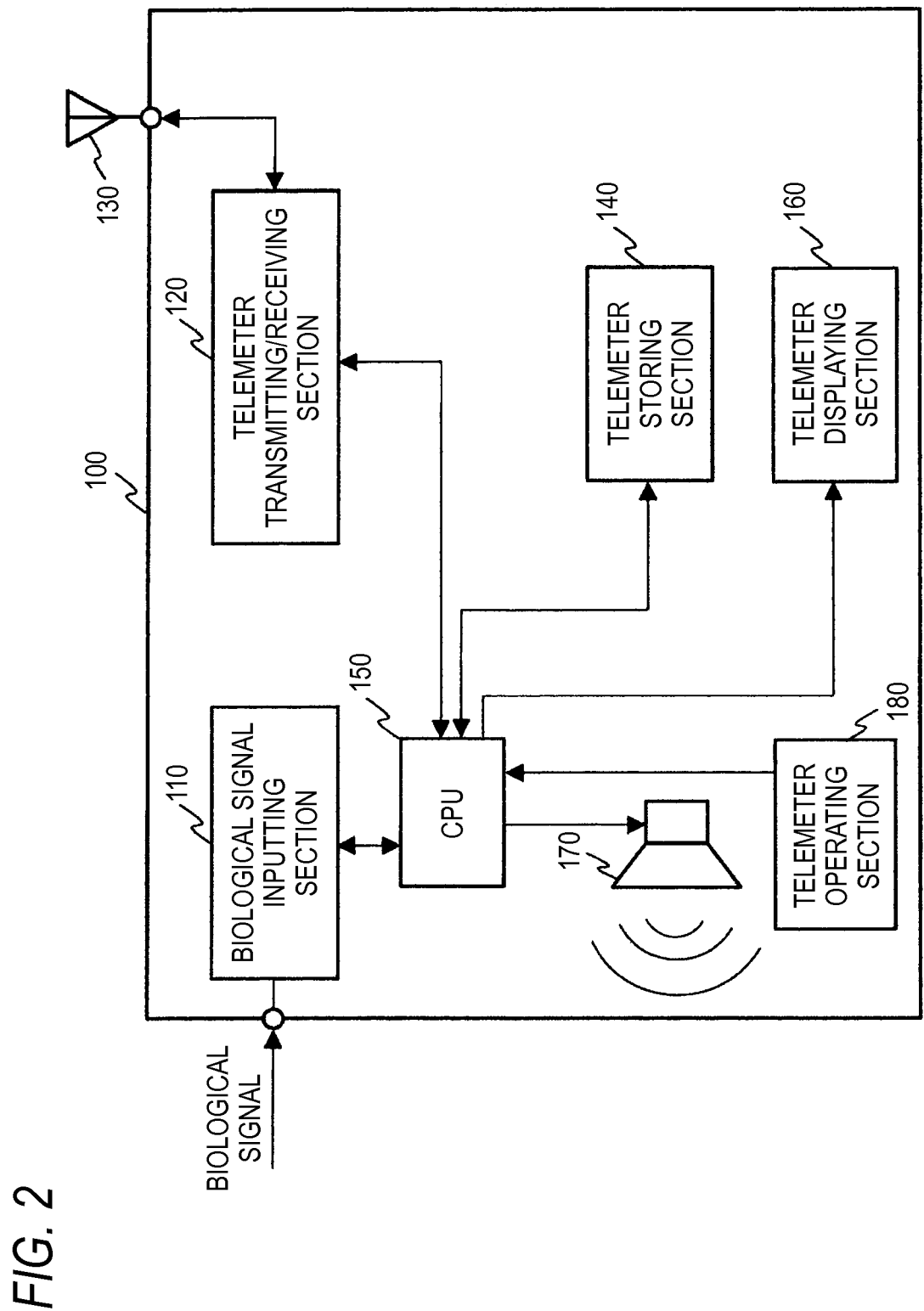
FIG. 2 is a block diagram showing the configuration of a medical telemeter 100 of Embodiment 1.

Each of the medical telemeters 100 is a device having a size and weight which allow a patient to carry the device. The configuration of the medical telemeter 100 will be described in detail with reference to FIG. 2. The medical telemeter 100 has a biological signal inputting section 110, a telemeter transmitting/receiving section 120, an antenna 130, a telemeter storing section 140, a CPU 150, a telemeter displaying section 160, a sound generator 170, and a telemeter operating section 180.

The biological signal inputting section 110 is electrically connected to electrodes, transducers, or the like attached to the patient, and receives measurement data output from these devices, such as an electrocardiogram, the respiratory rate, the blood pressure, and the pulse wave. The biological signal inputting section 110 supplies the input measurement data to the CPU 150.

The telemeter transmitting/receiving section 120 transmits the measurement data supplied from the biological signal inputting section 110, and various data supplied from the CPU 150 to the central monitor 200 through the antenna 130. The telemeter transmitting/receiving section 120 receives various data (including set values of patient information) transmitted from the central monitor 200. The telemeter transmitting/receiving section 120 supplies the received various data to the CPU 150.

The antenna 130 is a device which is used in the communication process with respect to the central monitor 200. For example, the antenna 130 is a WIFI antenna.

The telemeter storing section 140 is a storage device which stores various data including the set values of the patient information. For example, the telemeter storing section 140 may be a nonvolatile memory or a hard disk drive, or a memory which is configured so as to be detachable from the medical telemeter 100, such as a USB (Universal Serial Bus) memory. The telemeter storing section 140 has a concept including also a temporary storage device (for example, a cache memory) which is used by the CPU 150.

The patient information which is to be stored by the telemeter storing section 140 is information such as the name, ID, sex, age, and previous diseases of the patient who uses the medical telemeter 100. Namely, the patient information is information relating to the patient who uses the medical telemeter 100. The patient information may be input through the telemeter operating section 180 which will be described later, or set through the central monitor 200.

The CPU 150 (controller) controls the medical telemeter 100, and reads various programs from the telemeter storing section 140 to execute them. Moreover, the CPU 150 performs signal processes such as noise filtering and amplification on the measurement data supplied from the biological signal inputting section 110, and stores the processed measurement data in the telemeter storing section 140. The CPU 150 displays various waveforms and measurement values on the telemeter displaying section 160 by using the measurement data. When a predetermined event occurs, the CPU 150 further reads the patient information stored in the telemeter storing section 140, and controls the telemeter displaying section 160 so as to display a confirmation message corresponding to the readout patient information.

For example, a predetermined event which functions as a trigger for the display of a confirmation message may be one of the following cases:

(1) where setting of registration (or changing of setting) of patient information is received from another apparatus (preferably, the central monitor 200);

(2) where the power supply of the medical telemeter 100 is changed from turn-OFF to turn-ON; and (3) where a predetermined time period has elapsed after the previous display of a confirmation message, but patient information is not adequately set.

The above events (1) to (3) are mere examples. The medical telemeter 100 may be configured so that the administrator of the terminal can newly register the contents of events. The control of displaying the confirmation message will be described later in detail with reference FIGS. 4 to 9.

The telemeter displaying section 160 is a display device which is disposed on the housing of the medical telemeter 100, and which is configured by an LCD (Liquid Crystal Display), a CRT (Cathode Ray Tube), or the like. Measurement values (the respiratory rate and the like) of various biological parameters, the waveforms of biological signals, and the like are displayed on the telemeter displaying section 160. Under control of the CPU 150, a confirmation message for patient information (for example, the patient name) is further displayed on the telemeter displaying section 160.

The sound generator 170 is a speaker which emits electronic sound, a message, and the like toward the patient. Under control of the CPU 150, the sound generator 170 outputs an alarm informing of an abnormal condition of the patient. The sound generator 170 may output an alarm warning when patient information is not adequately set in the telemeter storing section 140.

The telemeter operating section 180 is an input interface which receives an input from the user (mainly, the patient, a nurse, or the like). For example, the telemeter operating section 180 is configured by buttons and the like disposed on the housing of the medical telemeter 100. The user inputs instructions for operations of stating or stopping measurements of various measurement parameters (for example, the body temperature, the SpO2, and the like), and starting or stopping of transmission of measured biological data, and the like, through the telemeter operating section 180. Alternatively, the telemeter operating section 180 may be configured so that patient information (for example, the patient name) can be input by operating the section.

A configuration in which the telemeter displaying section 160 and the telemeter operating section 180 are integrated with each other, i.e., a configuration similar to a touch panel may be employed.

Figure 3:
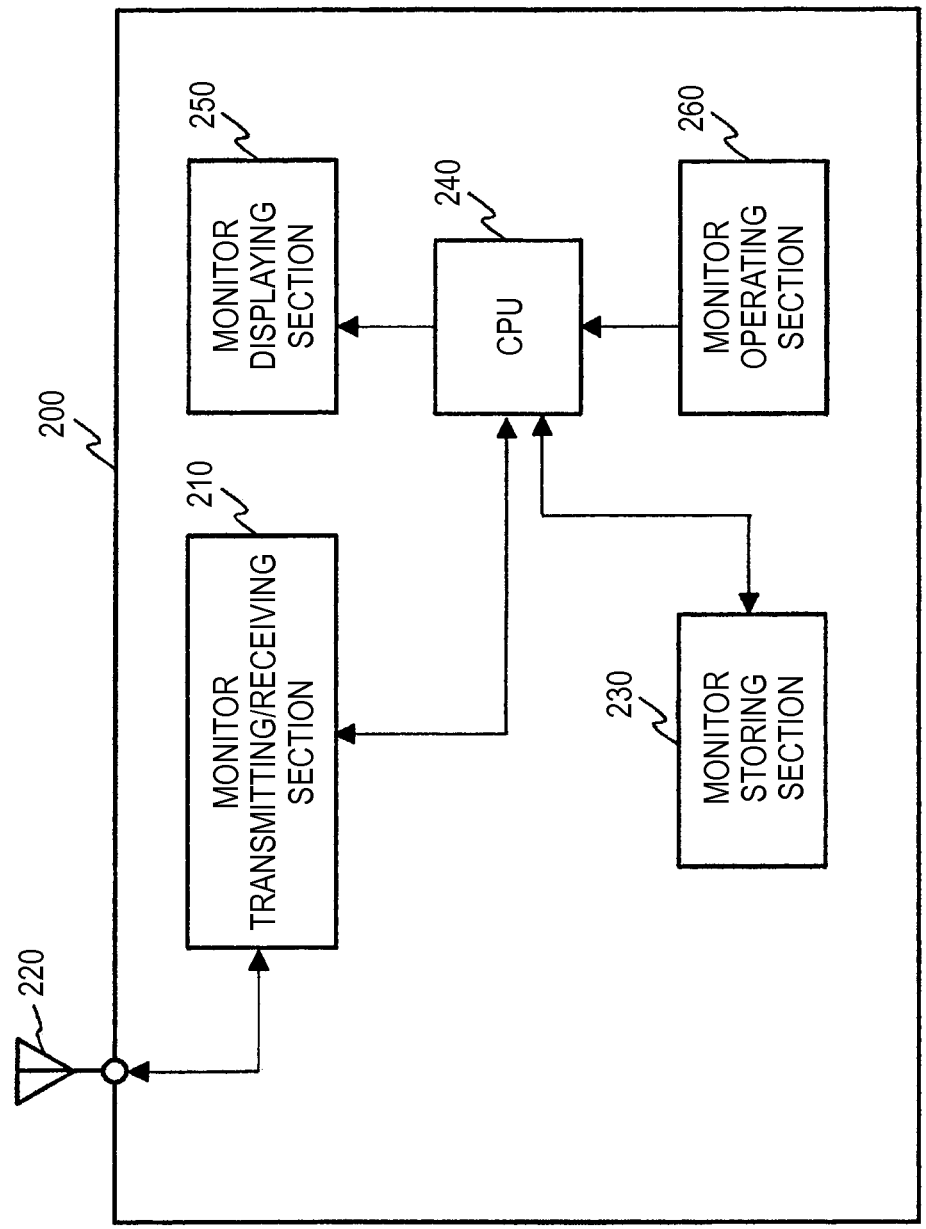
FIG. 3 is a block diagram showing the configuration of a central monitor 200 in Embodiment 1.

Referring to FIG. 3, then, the configuration of the central monitor 200 will be described. The central monitor 200 is configured so that it can transmit and receive data to and from the plurality of medical telemeters 100 (100-1 to 100-*n*). The central monitor 200 includes a monitor transmitting/receiving section 210, an antenna 220, a monitor storing section 230, a CPU 240, a monitor displaying section 250, and a monitor operating section 260. Also the central monitor 200 may have a configuration in which the monitor displaying section 250 and the monitor operating section 260 are integrated with each other, i.e., a configuration similar to a touch panel.

The monitor transmitting/receiving section 210 transmits and receives data to and from the medical telemeter 100 through the antenna 220. As described above, the central monitor 200 has the configuration where it can transmit and receive data to and from the plurality of medical telemeters 100-1 to 100-*n*. The monitor transmitting/receiving section 210 receives measurement data from the medical telemeters 100-1 to 100-*n*, and stores the received measurement data in the monitor storing section 230.

The monitor storing section 230 is a storage device which is disposed in the central monitor 200, and which stores measurement data of patients and the like. Preferably, the monitor storing section 230 is a hard disk drive incorporated in the central monitor 200.

The CPU 240 controls the central monitor 200, and reads various programs from the monitor storing section 230 to execute them. Moreover, the CPU 240 monitors measurement data of patients. In the case of an abnormal value, the CPU 240 causes the monitor displaying section 250 to display a warning message, or outputs an alarm through a speaker which is not shown. Moreover, the CPU 240 acquires the setting state of patient information in the medical telemeter 100 through the monitor transmitting/receiving section 210. Then, the CPU 240 causes the monitor displaying section 250 to display sets of patient information of the medical telemeters 100 (i.e., patients). An example of the display of the sets of patient information will be described later with reference to FIG. 10.

The monitor displaying section 250 is a display device which is disposed on the housing of the central monitor 200, and which is configured by an LCD (Liquid Crystal Display), a CRT (Cathode Ray Tube), or the like. Measurement values (the respiratory rate and the like) of patients (the medical telemeters 100), the waveforms of biological signals, and the like are displayed on the monitor displaying section 250.

The monitor operating section 260 is an input interface (for examples, buttons or a keyboard) which is disposed on the central monitor 200. The user (mainly, a nurse or a doctor) operates the monitor operating section 260 to set (or change) the patient information of the medical telemeter 100. The setting (or changing) operation will be described later with reference to FIG. 5.

Figure 4:
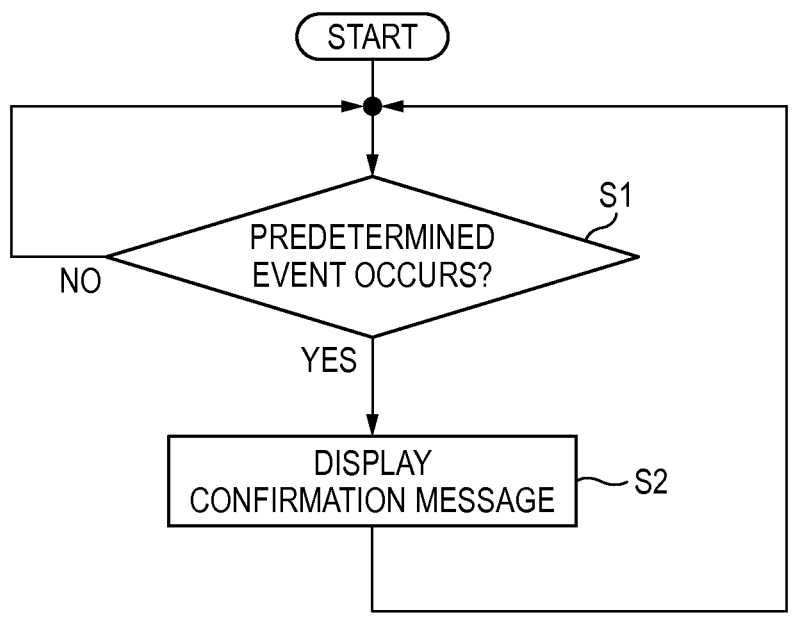
FIG. 4 is a flowchart showing a display control process of the medical telemeter 100 of Embodiment 1.

Then, the operation concept of the display of a confirmation message in the medical telemeter 100 will be described with reference to the flowchart of FIG. 4. The CPU 150 of the medical telemeter 100 always determines whether a predetermined event (for example, one of (1) to (3) above) occurs or not (S1). If a predetermined event occurs (S1: Yes), the CPU 150 reads the patient information from the telemeter storing section 140, and controls the telemeter displaying section 160 so as to display a confirmation message in which the read out patient information is used, on the telemeter displaying section (S2).

The confirmation message may be a fixed message such as "Patient name is ZZZZ" ("ZZZZ" is the read out patient name). Preferably, the confirmation message may be changed in accordance with the kind of the event which occurs in S1. An example of a confirmation message corresponding to the event will be described with reference to FIGS. 5 to 9.

Figure 5:
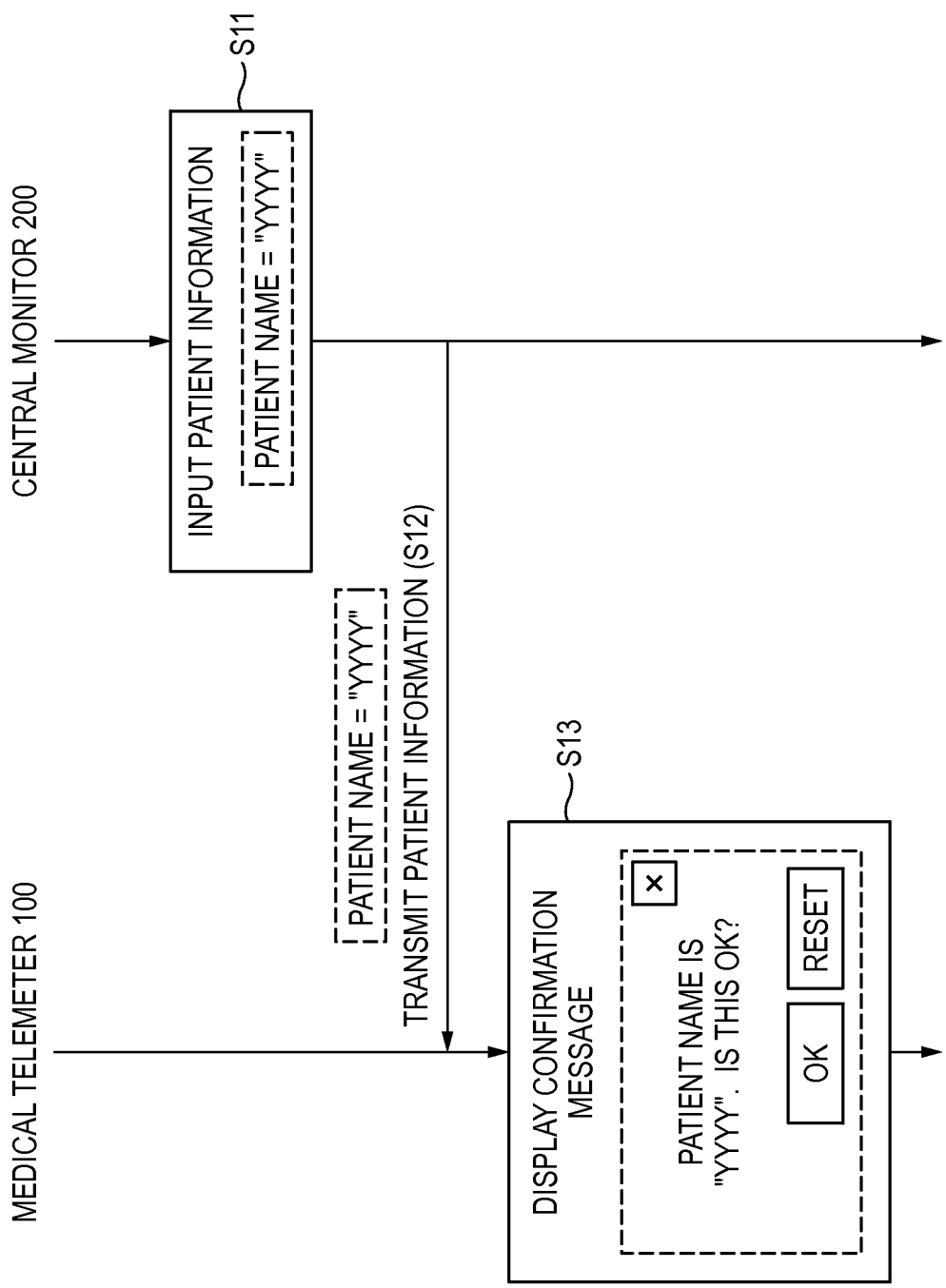
FIG. 5 is a diagram showing a process of displaying a confirmation message by the medical telemeter 100 of Embodiment 1.

Then, the process of displaying a confirmation message in the case where an event such as "The central monitor 200 sets patient information of the medical telemeter 100." ((1) above) occurs will be described with reference to FIG. 5. In FIG. 5 (and the subsequent figures), the solid lines indicate the operation of the medical telemeter 100 or the central monitor 200, and the broken lines indicate the confirmation message displayed on the telemeter displaying section 160, or the patient information stored in the telemeter storing section 140.

The user (mainly, a nurse) operates the monitor operating section 260 to set the patient information of the medical telemeter 100 (S11). In the following description, it is assumed that "Patient name" is set as patient information. In the example of FIG. 5, the user sets "YYYY" as the patient name. The central monitor 200 transmits the set patient information (PATIENT NAME="YYYY") to the medical telemeter 100 (S12).

The telemeter transmitting/receiving section 120 receives the patient information transmitted from the central monitor 200 (S12). The CPU 150 writes the received patient information to the telemeter storing section 140 (S12). While using the event (the process of receiving patient information, and writing the patient information to the telemeter storing section 140) as a trigger, the CPU 150 reads the patient information from the telemeter storing section 140, and displays a confirmation message which is produced based on the read out patient information, on the telemeter displaying section 160 (S13). In the example of FIG. 5, a confirmation message "Patient name is "YYYY" Is this OK?" is displayed on the telemeter displaying section 160 (S13). In the case where "Reset" button is depressed in a pop-up window of the confirmation message, the medical telemeter 100 controls so as to perform resetting of patient information through the telemeter operating section 180 or the central monitor 200.

Figure 6:
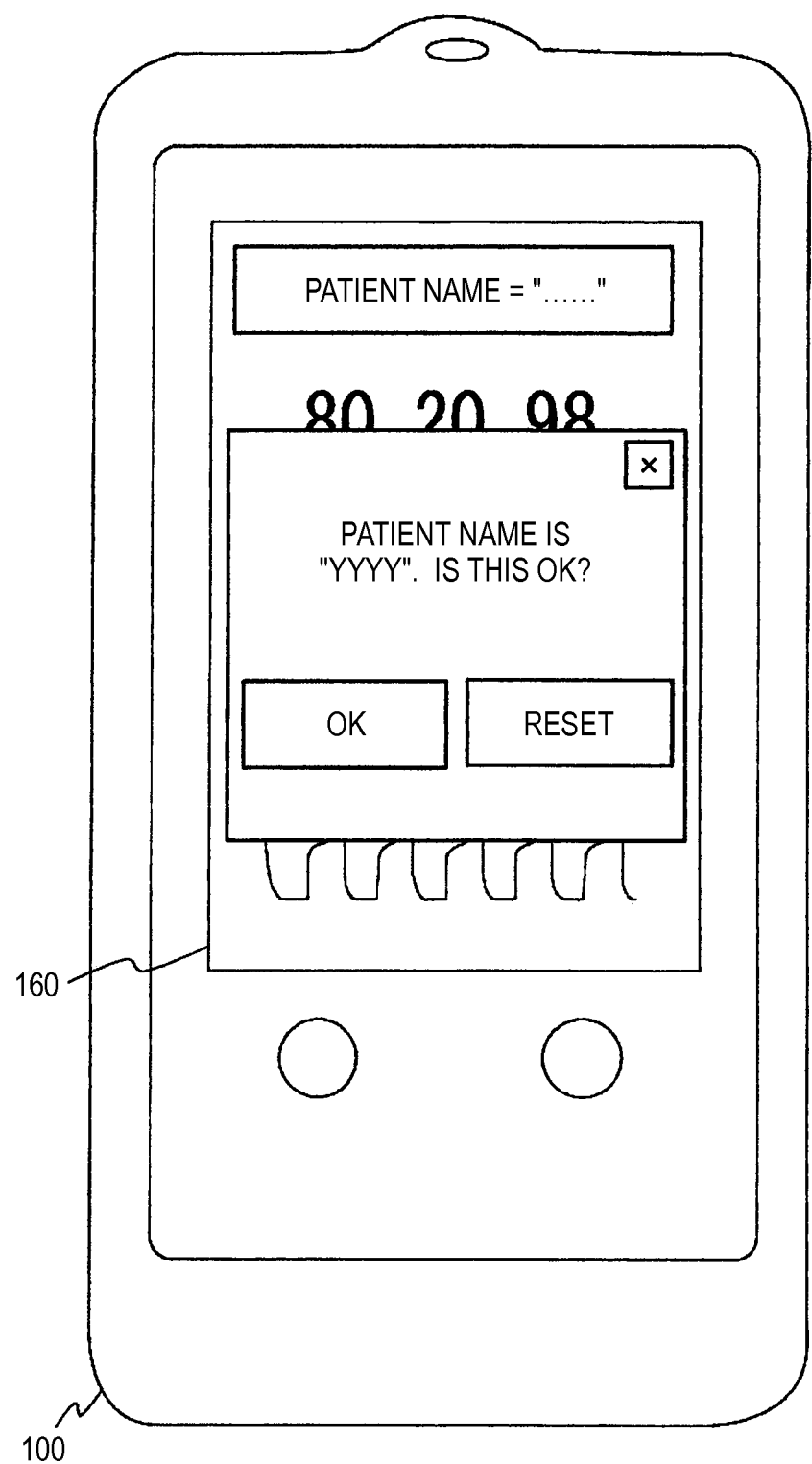
FIG. 6 is a view showing the process of displaying the confirmation message by the medical telemeter 100 of Embodiment 1.

For example, FIG. 6 shows a display of an actual telemeter. FIG. 6 is a conceptual view showing the appearance of the medical telemeter 100 and a display example of the telemeter displaying section 160. As illustrated, a confirmation message from which the set patient name is known is displayed in a pop-up window on a screen.

Figure 7:
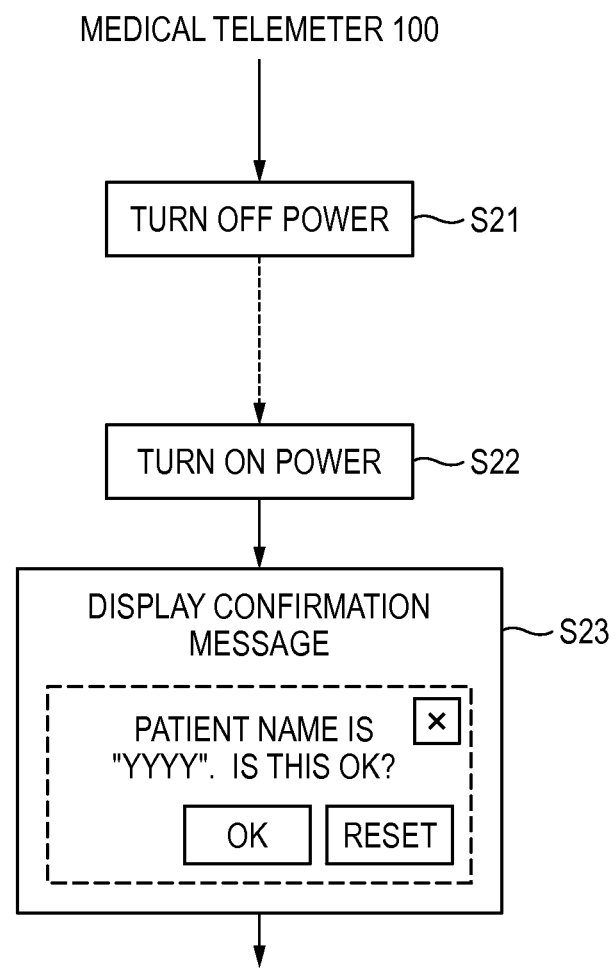
FIG. 7 is a diagram showing the process of displaying the confirmation message by the medical telemeter 100 of Embodiment 1.

Then, the process of displaying a confirmation message in the case where an event "The power supply of the medical telemeter 100 is changed from turn-OFF to turn-ON." ((2) above) occurs will be described with reference to FIG. 7.

It is assumed that the power supply is turned OFF by the user of the medical telemeter 100 (S21). Thereafter, the user of the medical telemeter 100 turns ON the power supply (S22). While using the event of the turning-ON of the power supply (S22) as a trigger, the CPU 150 of the medical telemeter 100 performs the process of displaying a confirmation message (S23). Specifically, the CPU 150 reads the set value of the patient name from the telemeter storing section 140, and displays a confirmation message in which the read out patient name is used, on the telemeter displaying section 160. In the example of FIG. 7, "Patient name is "YYYY". Is this OK?" is displayed as a confirmation message.

The message control may be performed based on the length of the time period when the medical telemeter 100 is powered OFF. This message control will be described in detail with reference to FIGS. 8A and 8B.

When the power-OFF operation is performed, the medical telemeter 100 records the date and time when the operation is performed, as the final operation date and time in the telemeter storing section 140 (S31, S41). An unexpected power-OFF operation may be sometimes caused due to battery exhaustion. Therefore, the medical telemeter 100 may record the date and time when the battery residual quantity is equal to or less than a predetermined value (for example, 30 minutes before battery exhaustion), as the final operation date and time. Thereafter, the user of the medical telemeter 100 turns ON the power supply (S32). The CPU 150 determines whether the difference between the current date and time (the date and time when the power supply is turned ON) and the final operation date and time is within a predetermined time period (for example, within 48 hours) or not.

If the difference is within the predetermined time period (FIG. 8A), the CPU 150 reads the patient information from the telemeter storing section 140, and produces a confirmation message. In the example of FIG. 8(A), the confirmation message "Patient name is "YYYY." Is this OK?" is displayed (S33). That is, in the case where an event "After a power-OFF state for a short time period, the state transits to the power-ON state." occurs, the CPU 150 displays a confirmation message in which the read out patient name is used.

By contrast, if the time period when the power supply is turned OFF is equal to or longer than the predetermined time period (FIG. 8B), the CPU 150 reads the patient information from the telemeter storing section 140, and produces a confirmation message with using the read out patient information from which the patient name is excluded. In the example of FIG. 8B, a confirmation message "Male of 59 years old is set as user of medical telemeter" is displayed (S43). In this way, in the case where there is a high possibility that the patient who uses the medical telemeter 100 was changed to another patient, a confirmation message using information from which the former patient cannot be identified is produced. Namely, in the case where an event "After a power-OFF state for a long time period, the state transits to the power-ON state." occurs, the CPU 150 displays a confirmation message in which patient information other than the patient name is used.

Figure 9:
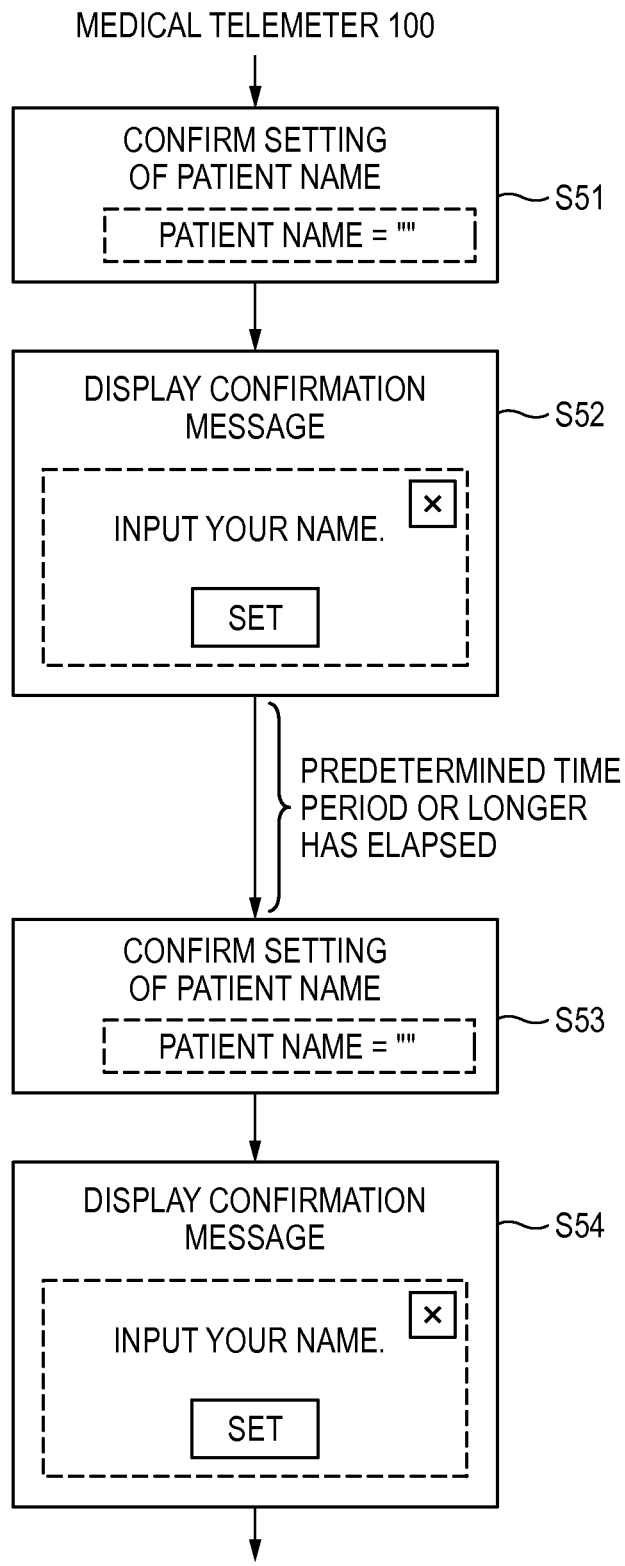
FIG. 9 is a diagram showing the process of displaying the confirmation message by the medical telemeter 100 of Embodiment 1.

Then, the process of displaying a confirmation message in the case where an event "A predetermined time period has elapsed while the patient name remains unset." ((3) above) occurs will be described with reference to FIG. 9. In the case where the power supply is changed to turn-ON (identical with the case of FIG. 7), for example, the CPU 150 reads the patient information from the telemeter storing section 140. In the example of FIG. 9, it is assumed that the patient name is not set (S51). Therefore, the CPU 150 displays a confirmation message for prompting the setting of the patient name ("Input your name") (S52).

After elapse of a predetermined time period (for example, one minute) from the display of the confirmation message, the CPU 150 determines whether the patient information is adequately set or not (S53). In the example of FIG. 9, the patient name remains unset. Therefore, the CPU 150 again displays the confirmation message for prompting the setting of the patient name (S54).

In the above, the example of the display of the confirmation message has been described. Alternatively, the CPU 150 may control the sound generator 170 so that, when the confirmation message is displayed, an alarm is simultaneously sounded. In the case where an alarm is sounded, the alarm sound may be changed in accordance with the kind of the displayed confirmation message.

Figure 10:
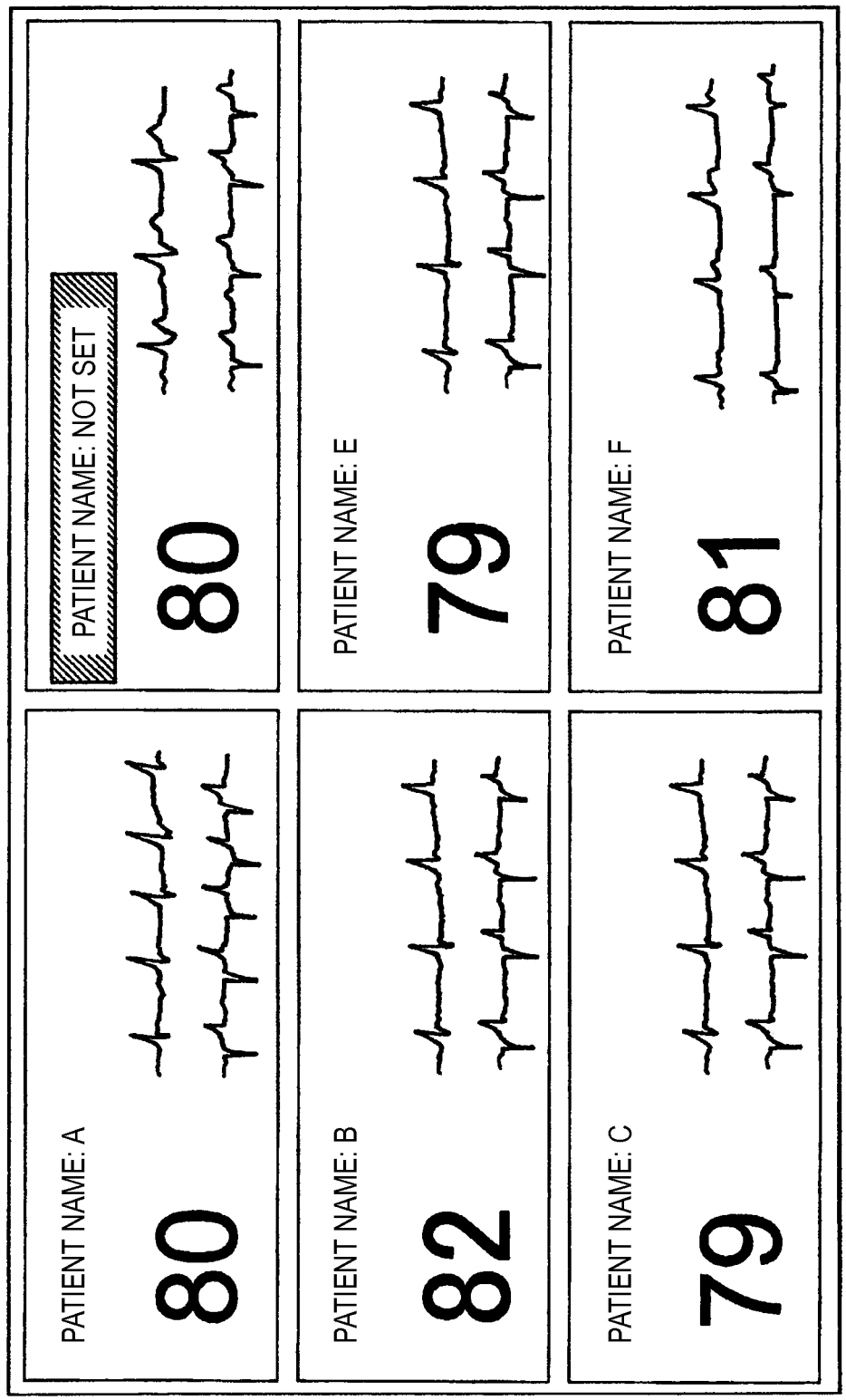
FIG. 10 is a view showing an example of a display screen of the central monitor 200 in Embodiment 1.

Also an example of the display on the side of the central monitor 200 will be described with reference to FIG. 10. As described above, the central monitor 200 and the medical telemeters 100 (100-1 to 100-n) communicate with each other by using the wireless communication function. The medical telemeter 100 notifies the central monitor 200 of the set contents of the patient information in the own telemeter, together with the measurement data. The CPU 240 of the central monitor 200 controls the monitor displaying section 250 so as to display the measurement data and set contents of the patient information respectively corresponding to the medical telemeters 100-1 to 100-n. FIG. 10 shows an example of the monitor screen.

The CPU 240 determines whether the patient information of the medical telemeters 100-1 to 100-n is adequately set or not. If, in a certain one of the medical telemeters, the patient information is not adequately set, the field for displaying the patient name and the like in the medical telemeter is highlight displayed (the hatched portion in FIG. 10). Therefore, the user (mainly, a nurse) of the central monitor 200 can easily know that the patient information is not adequately set.

Then, the effects of the medical system 10 and medical telemeter 100 of the embodiment will be described. The medical telemeter 100 manages patient information, and, in the case where an event (for example, the events (1) to (3) above) in which the patient information is better to be confirmed occurs, displays a confirmation message corresponding to the patient information. Therefore, the user of the medical telemeter 100 can confirm whether the patient information (for example, the patient name) is adequately set or not. If the patient information is not adequately set, the setting can be changed. Consequently, it is ensured that patient information is adequately set in the medical telemeter 100, and it is possible to remarkably reduce the possibility that troubles such as that a patient is misidentified occur.

As shown in FIGS. 5 to 9, the CPU 150 changes the contents of the confirmation message in accordance with the kind of an event (for example, the events (1) to (3) above) in which patient information is better to be confirmed. Therefore, the user of the medical telemeter 100 can adequately know the detail of the set contents of the patient information, and the manner of responding to the message. In the case where the patient information is not adequately set, for example, the CPU 150 displays a confirmation message for prompting an input (FIG. 9). According to the configuration, the user of the medical telemeter 100 (or a nurse or the like who is responsible for the user) can promptly input the patient information.

When a confirmation message is displayed, the medical telemeter 100 may output an alarm sound. According to the configuration, the user of the medical telemeter 100 can know more surely the set state of the patient information.

The medical telemeter 100 may store the final operation date and time in response to the turning ON/OFF of the power supply, and control so as not to display the patient name according to whether the time period when the power supply is turned OFF is equal to or longer than the predetermined time period or not (FIGS. 8A and 8B). In the medical telemeter 100 which has not been used for a long time period, there is a high possibility that the patient who uses the medical telemeter 100 was changed to another patient. In this case, when the name of the former patient is displayed, a problem is caused from the viewpoint of privacy. In the case where the above-described control (FIGS. 8(A) and 8(B)) is performed, even when the medical telemeter 100 has not been used for a long time period, however, it is possible to confirm the set state of the patient information without identifying the patient name.

Moreover, the medical telemeter 100 may manage the date and time when the battery residual quantity is equal to or less than a predetermined time period (predetermined value), as the final operation date and time. According to the configuration, even when operation interruption occurs due to sudden battery exhaustion, it is possible to display an adequate confirmation message.

Although the presently disclosed subject matter has been specifically described based on the embodiment, the presently disclosed subject matter is not limited to the above-described embodiment, and it is a matter of course that various changes can be made without departing from the spirit of the presently disclosed subject matter.

In the above description, a confirmation message is produced based on the patient information which is read out from the telemeter storing section 140. In the case where the patient name is not set, for example, the confirmation message "Input your name" (FIG. 9) is displayed; in the case where the patient name is set, "Patient name is "YYYY". Is this OK?" (FIG. 5) is displayed; and, in the case where the power supply is turned OFF for a long time period, "Male of 59 years old is set as user of medical telemeter" (FIG. 8B) in which the patient information other than the patient name is used is displayed.

In the case where the power-OFF state is continued for a long time period, alternatively, the CPU 150 may produce a confirmation message without referring to the patient information. The CPU 150 detects that the power-OFF state is continued for a predetermined time period or longer. In the case where that the power-OFF state is continued for three days or longer, for example, a confirmation message "Reset patient information" may be displayed.

When the power-OFF state is continued for a long time period, there is a high possibility that the patient who uses the medical telemeter 100 was changed to another patient. In the case where the power-OFF state is continued for a predetermined time period or longer, therefore, the patient information is forcedly reset, so that the patient information is maintained in a correct state.

The processes of the CPU 150 may be realized as computer programs which operate in the medical telemeter 100. Similarly, the processes of the CPU 240 may be realized as computer programs which operate in the central monitor 200. The programs may be stored in a non-transitory computer readable medium of any one of various types, and then supplied to the computer. The non-transitory computer readable medium includes tangible storage media of various types. Examples of the non-transitory computer readable medium are a magnetic recording medium (for example, a flexible disk, a magnetic tape, and a hard disk drive), a magneto-optical recording medium (for example, a magneto-optical disk), a CD-ROM (Read Only Memory), a CD-R, a CD-R/W, a semiconductor memory (for example, a mask ROM, a PROM (Programmable ROM), an EPROM (Erasable PROM), a flash ROM, and a RAM (Random Access Memory)). Alternatively, the programs may be supplied to the computer by means of a transitory computer readable medium of any one of various types. Examples of the transitory computer readable medium are an electrical signal, an optical signal, and an electromagnetic wave. The transitory computer readable medium can supply the programs to the computer through a wired communication path such as a metal wire or an optical fiber, or a wireless communication path.

According to the presently disclosed subject matter, in the case where an event in which patient information is better to be confirmed occurs, a confirmation message corresponding to the patient information is displayed on the displaying section. According to the configuration, the user of the medical telemeter can confirm whether the patient information (for example, the patient name) is adequately set or not. If the patient information is not adequately set, the setting can be changed. Therefore, it is ensured that patient information is adequately set in the medical telemeter.

According to the presently disclosed subject matter, it is possible to provide a medical telemeter, medical system, and method of controlling a medical telemeter in which set patient information can be adequately confirmed.

What is claimed is:

1. A medical telemeter comprising:
a receiving section which is configured to receive, from an external computer, contents of patient information set through an input interface of the external computer, the patient information being information of a patient who uses the medical telemeter;
a displaying section which is configured to display the contents of the patient information, which is received from the external computer;
a storing section which is configured to store the contents of the patient information, which is received from the external computer; and
a controller which is configured to: determine whether a predetermined event occurs, and when it is determined that the predetermined event occurs, read the patient information stored in the storing section, cause the displaying section to display a confirmation message that is based on the patient information, and change contents of the confirmation message in accordance with a kind of the predetermined event,
wherein the predetermined event includes an event in which setting of the patient information or changing of the setting of the patient information is received from the external computer.

2. The medical telemeter according to claim 1, further comprising a sound generator which, when the confirmation message is displayed, is configured to output an alarm sound.

3. The medical telemeter according to claim 1, wherein the controller is configured to control the storing section to store a date and time when a power supply of the medical telemeter is turned OFF, as a final operation date and time, and is configured to change the contents of the confirmation message in accordance with whether a difference between the final operation date and time and a date and time when the power supply is turned ON is equal to or less than a predetermined time period.

4. The medical telemeter according to claim 3, wherein the controller is configured to write a date and time when a battery residual quantity of the medical telemeter is equal to or less than a predetermined value, as the final operation date and time in the storing section.

5. The medical telemeter according to claim 1, wherein the patient information includes at least information of a name of the patient.

6. The medical telemeter according to claim 5, wherein the confirmation message is a message for confirming whether the patient information is adequately set in the medical telemeter or a message for prompting a user to confirm the patient information that has been set in the medical telemeter.

7. The medical telemeter according to claim 5, wherein the predetermined event includes at least one of cases:
where although a predetermined time period has elapsed from a previous display of the confirmation message, the patient information is not adequately set; and
where a power supply of the medical telemeter is turned OFF, and then switched to an ON state.

8. A medical telemeter comprising:
a displaying section which is configured to display information; and
a controller which is configured to control a storing section to store a date and time when a power supply of the medical telemeter is turned OFF, and which is configured to detect a difference between a date and time when the power supply of the medical telemeter is turned ON and the stored date and time when the power supply of the medical telemeter is turned OFF, the controller which is configured to compare the difference and a predetermined time period, and which, when the difference is longer than the predetermined time period, is configured to cause the displaying section to display a confirmation message for prompting re-inputting of patient information.

9. A medical system which includes a medical telemeter and a central monitor which are configured to mutually transmit and receive data, the central monitor comprising:
an input interface configured for setting contents of patient information that is information of a patient who uses the medical telemeter;
a memory that stores the set contents of patient information; and
a transmitting section that transmits the set contents of patient information to the medical telemeter, and
the medical telemeter comprising:
a receiving section that receives the set contents of patient information from the central monitor;
a displaying section which is configured to display the set contents of patient information received from the central monitor on a monitor screen;
a storing section which is configured to store the set contents of patient information received from the central monitor that is information of a patient who uses the medical telemeter; and
a controller which, when a predetermined event occurs, is configured to read the patient information stored in the storing section, and is configured to cause the displaying section to display a confirmation message that is based on the patient information.

10. The medical system according to claim 9, wherein,
when the set contents of the patient information which are transmitted from the medical telemeter are not adequate, a display field of the medical telemeter is highlight-displayed.

11. A medical telemeter, comprising:
a displaying section which is configured to display information;
a storing section which is configured to store patient information that is information of a patient who uses the medical telemeter; and
a controller which is configured to: determine whether a predetermined event occurs, and
when it is determined that the predetermined event occurs, read the patient information stored in the storing section, and cause the displaying section to display a confirmation message that is based on the patient information, wherein
the predetermined event includes a case where a difference between a date and time when a power supply of the medical telemeter is turned OFF and a date and time when the power supply of the medical telemeter is turned ON satisfies a predetermined condition.

12. A medical telemeter comprising:
a displaying section which is configured to display information;
a storing section which is configured to store patient information that is information of a patient who uses the medical telemeter; and
a controller which is configured to: determine whether a predetermined event occurs, and when it is determined that predetermined event occurs, read the patient information stored in the storing section, and cause the displaying section to display a confirmation message that is based on the patient information, wherein
the predetermined event includes a case where a power supply of the medical telemeter is turned OFF, and then switched to an ON state.

* * * * *